(12) United States Patent
Yang et al.

(10) Patent No.: US 11,250,599 B2
(45) Date of Patent: Feb. 15, 2022

(54) METHOD OF REGULARIZATION DESIGN AND PARAMETER TUNING FOR DYNAMIC POSITRON EMISSION TOMOGRAPHY IMAGE RECONSTRUCTION

(71) Applicant: CANON MEDICAL SYSTEMS CORPORATION, Otawara (JP)

(72) Inventors: Li Yang, Vernon Hills, IL (US);
Wenyuan Qi, Vernon Hills, IL (US);
Evren Asma, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/857,916

(22) Filed: Apr. 24, 2020

(65) Prior Publication Data

US 2021/0335022 A1    Oct. 28, 2021

(51) Int. Cl.
*G06T 11/00*  (2006.01)
*A61B 6/03*  (2006.01)

(52) U.S. Cl.
CPC .............. *G06T 11/005* (2013.01); *A61B 6/037* (2013.01); *G06T 2210/41* (2013.01)

(58) Field of Classification Search
CPC ... G06T 7/0012; G06T 11/003; G06T 11/005; G06T 11/006; G06T 11/008; G06T 2207/10104; G06T 2210/41; A61B 6/037; A61B 6/5205; A61B 6/5217; G01N 2223/108; G01T 1/2985

See application file for complete search history.

(56) References Cited

U.S. PATENT DOCUMENTS

| 2009/0154641 A1* | 6/2009 | Thielemans | .......... G01T 1/1647 |
| | | | 378/21 |
| 2015/0363948 A1* | 12/2015 | Leahy et al. | .......... G06T 11/006 |
| | | | 600/425 |
| 2019/0365341 A1 | 12/2019 | Chan et al. | .......... A61B 6/5258 |

(Continued)

FOREIGN PATENT DOCUMENTS

WO      2018/099772 A1      6/2018      ............. G06T 11/00

OTHER PUBLICATIONS

Li Yang, "Penalized Maximum-likelihood PET Image Reconstruction for Lesion Detection", Phd Thesis Defense, Biomedical Engineering, https://docplayer.net/104526482-Penalized-maximum-likeiihood-pet-image-reconstruction-for-lesion-detection-b-i-o-m-e-d-i-c-a-l-e-n-g-i-n-e-e-r-i-n-g-li-yang-advisor-prof.html, Apr. 6, 2015, 71 pages.

(Continued)

*Primary Examiner* — Andrew W Johns
(74) *Attorney, Agent, or Firm* — Oblon, McClelland, Maier & Neustadt, L.L.P.

(57) ABSTRACT

A method of imaging includes obtaining a plurality of dynamic sinograms, each dynamic sinogram representing detection events of gamma rays at a plurality of detector elements, summing the plurality of dynamic sinograms to generate an activity map based on a radioactivity level of the gamma rays; reconstructing, using the plurality of dynamic sinograms, a plurality of dynamic images, each of the plurality of dynamic images corresponding to one of the each of the plurality of dynamic sinograms, and generating, using the plurality of dynamic sinograms and the activity map, at least one parametric image.

20 Claims, 4 Drawing Sheets

(56) References Cited

U.S. PATENT DOCUMENTS

2020/0105032 A1    4/2020   Yang et al. ........... G06T 11/006

OTHER PUBLICATIONS

Li Yang, et al., "Theoretical Analysis of Lesion Detectability in Penalized Maximum-likelihood Patlak Parametric Image Reconstruction Using Dynamic PET", IEEE 12th International Symposium on Biomedical Imaging (ISBI), Apr. 16-19, 2015, pp. 1188-1191.

Guobao Wang, et al., "Direct Estimation of Kinetic Parametric Images for Dynamic PET", Theranostics, vol. 3, Issue 10, Nov. 10, 2013, pp. 802-815.

Guobao Wang, et al., "Penalized Likelihood PET Image Reconstruction Using Patch-Based Edge-Preserving Regularization", IEEE Transactions on Medical Imaging, vol. 31, No. 12, Dec. 2012, pp. 2194-2204.

Guobao Wang, et al., "Maximum a posteriori reconstruction of the Patlak parametric image from sonograms in dynamic PET", Institute of Physics and Engineering in Medicine, Physics in Medicine & Biology, vol. 53, No. 3, Feb. 7, 2008, pp. 593-604 (Abstract only).

Guobao Wang, et al., "Generalized Algorithms for Direct Reconstruction of Parametric Images from Dynamic PET Data", IEEE Transactions on Medical Imaging, vol. 28, No. 11, Nov. 2009, pp. 1717-1726.

Li Yang, et al., "Theoretical analysis of penalized maximum-likelihood Patlak parametric image reconstruction in dynamic PET for lesion detection", IEEE Transactions on Medical Imaging, vol. 35, No. 4, Apr. 2016, pp. 947-956.

Extended European Search Report dated Sep. 27, 2021 in corresponding European Patent Application No. 21170232.9, 8 pages.

\* cited by examiner

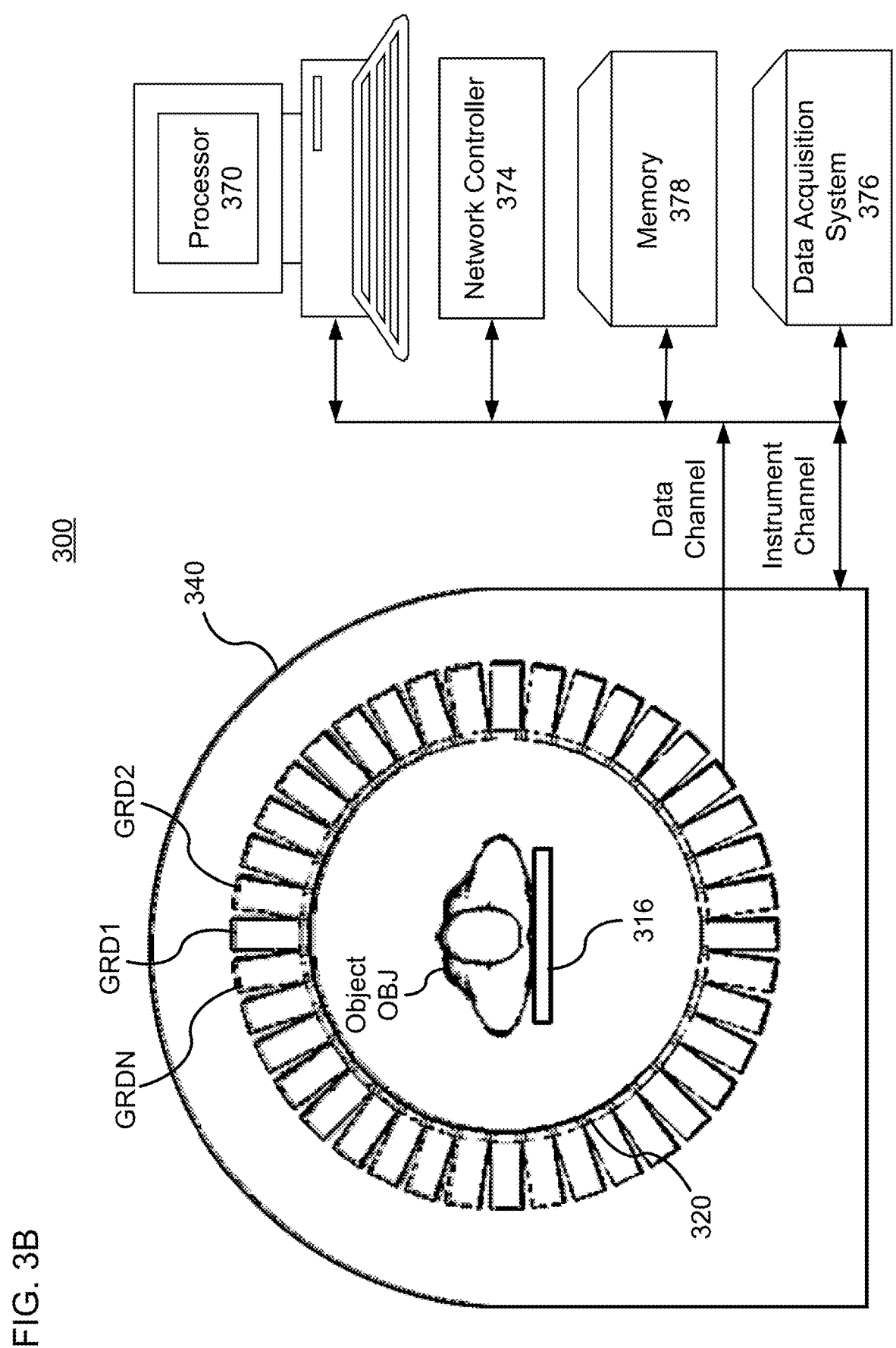

METHOD OF REGULARIZATION DESIGN AND PARAMETER TUNING FOR DYNAMIC POSITRON EMISSION TOMOGRAPHY IMAGE RECONSTRUCTION

FIELD OF THE INVENTION

This disclosure relates to tomographic image reconstruction in which parametric fitting is performed on dynamic images to produce parametric images, and, more particularly, to positron emission tomography (PET) parametric image generation using Patlak fitting with a penalty function based on an activity map.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Positron emission tomography (PET) is a functional imaging modality that is capable of imaging biochemical processes in humans or animals through the use of radioactive tracers. In PET imaging, a tracer agent is introduced into the patient to be imaged via injection, inhalation, or ingestion. After administration, the physical and bio-molecular properties of the agent cause it to concentrate at specific locations in the patient's body. The actual spatial distribution of the agent, the intensity of the region of accumulation of the agent, and the kinetics of the process from administration to its eventual elimination are all factors that may have clinical significance.

The most commonly used tracer for PET studies is fluorodeoxyglucose (FDG), which allows the study of glucose metabolism, a process that is up-regulated substantially in cancerous tissue. PET scans with FDG are increasingly being used for staging, restaging, and treatment monitoring for cancer patients with different types of tumors.

During this process, a tracer attached to the agent will emit positrons. When an emitted positron collides with an electron, an annihilation event occurs, wherein the positron and electron are combined. Most of the time, an annihilation event produces two gamma rays (at 511 keV) traveling at substantially 180 degrees apart.

To reconstruct the spatio-temporal distribution of the tracer via tomographic reconstruction principles, each detected event is characterized for its energy (i.e., amount of light generated), its location, and its timing. By detecting the two gamma rays, and drawing a line between their locations, i.e., the line-of-response (LOR), one can determine the likely location of the original disintegration. While this process will only identify a line of possible interaction, by accumulating a large number of those lines, tomographic reconstruction can be used to estimate the original distribution. Thus, the LOR for coincidence pairs and the timing information is used to reconstruct a tomographic image of the radioactivity, yielding clinical information.

However, the potential of PET is under-utilized by current routine static imaging protocols, which mainly examine the tracer concentration at a single time point. It is reasonable to expect that dynamic PET, which follows the tracer uptake over a period of time, would provide more accurate information than static PET. Also, the recent development of PET scanners with increased axial field-of-view (FOV) makes the whole-body dynamic imaging possible for routine clinical practice.

One popular method to analyze dynamic PET data is the Patlak graphical model. The slope of the Patlak plot and the corresponding parametric images has proven to be an effective quantitative index for characterizing kinetic properties of many PET tracers. In some methods, a penalty function may be applied to the Patlak fitting. Properly tuning the penalty strength and penalty parameters to fully take advantage of the spatial-temporal information in dynamic PET data is a challenge and contributes to achieving desired performances in reconstructed images. Thus, a method including an optimal penalty function for dynamic PET that is able to exploit spatial information embed in dynamic PET data to suppress noise while preserving image features (e.g. fine structures and sharp edges around organ boundaries) in the parametric images is desired.

SUMMARY

The present disclosure relates to an apparatus, including: circuitry configured to obtain a plurality of dynamic sinograms, each dynamic sinogram representing detection events of gamma rays at a plurality of detector elements, sum the plurality of dynamic sinograms to generate an activity map based on a radioactivity level of the gamma rays, reconstruct, using the plurality of dynamic sinograms, a plurality of dynamic images, each of the plurality of dynamic images corresponding to one of the each of the plurality of dynamic sinograms, and generate, using the plurality of dynamic sinograms and the activity map, at least one parametric image.

The disclosure additionally relates to a method of imaging, including: obtaining a plurality of dynamic sinograms, each dynamic sinogram representing detection events of gamma rays at a plurality of detector elements; summing the plurality of dynamic sinograms to generate an activity map based on a radioactivity level of the gamma rays; reconstructing, using the plurality of dynamic sinograms, a plurality of dynamic images, each of the plurality of dynamic images corresponding to one of the each of the plurality of dynamic sinograms; and generating, using the plurality of dynamic sinograms and the activity map, at least one parametric image.

Note that this summary section does not specify every embodiment and/or incrementally novel aspect of the present disclosure or claimed invention. Instead, this summary only provides a preliminary discussion of different embodiments and corresponding points of novelty. For additional details and/or possible perspectives of the invention and embodiments, the reader is directed to the Detailed Description section and corresponding figures of the present disclosure as further discussed below.

BRIEF DESCRIPTION OF THE DRAWINGS

Various embodiments of this disclosure that are proposed as examples will be described in detail with reference to the following figures, wherein like numerals reference like elements, and wherein:

FIG. 3B shows a schematic view of a PET scanner, according to an embodiment of the present disclosure.

DETAILED DESCRIPTION

Figure 1:
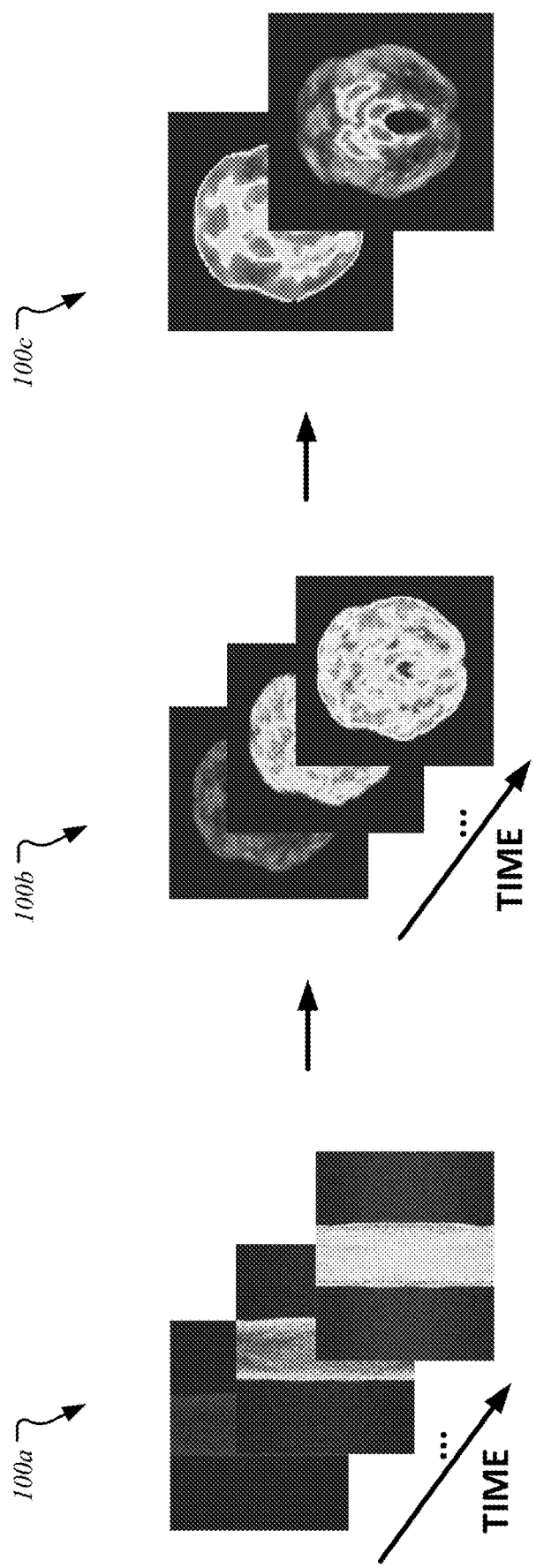
FIG. 1 shows reconstruction of dynamic emission images and parametric fitting of the dynamic emission images to generate parametric images, according to an embodiment of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed. Further, spatially relative terms, such as "top," "bottom," "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The order of discussion of the different steps as described herein has been presented for clarity sake. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

Some methods for generating parametric images during dynamic PET include reconstructing dynamic emission images from dynamic sinogram data and then perform Patlak analysis on the time activity curves (TAC) to generate parametric images, which can be referred to as an indirect method. However, the indirect method can be sensitive to the noise which greatly degrades the image quality in the final parametric images.

In some methods, a direct reconstruction can reconstruct the Patlak parametric images from dynamic sinogram data by incorporating the Patlak model into the image reconstruction procedure. Unfortunately, the direct methods can prove more complex and time-consuming than the indirect method which can limit its practical use. For example, a quadratic penalty can be applied to a frame-by-frame reconstruction and the Patlak parametric image estimations to maximize lesion detection performance. However, this method can limit the freedom to tune the penalty strength according to any other rule and may not include the option to change the penalty type/parameters from one region to another.

As described herein, a regularization method is incorporated in dynamic PET reconstruction including regularization/penalty parameter selection where a spatially variant map can be determined for the penalty type, parameter, and strength based on an estimated activity map of combined dynamic scan data.

The methods described herein can improve the quality of PET images by spatially varying the penalty function during a parametric fitting based on an activity-level mapping derived from a reconstructed image. In an embodiment, the method utilizes activity estimates by reconstructing measured emission data summed over a predetermined scan duration to guide a smoothing strength in dynamic reconstruction. The optimal degree of penalty can depend the level of activity in a given image. That is, different images with different amounts of activity can benefit from having different degrees of penalty. Further, this idea can carryover and apply to different regions within an image. That is, a region with a greater level of activity can benefit from a different degree of penalty than a region with a lesser level of activity. The smoothing strength based on static reconstruction can be applied both in the frame-by-frame reconstruction, and the voxel- or pixel-based Patlak model fitting. While the penalty type and parameters, such as the edge-preservation parameter, can also be changed, the parameter of interest is the smoothing strength and how it can be changed based on activity, and imposed on dynamic parametric images. Thus, the method allows scaling of the penalty term according to any desired function of activity.

In an embodiment, the activity-dependent smoothing parameter scaling can also be used in combination with other smoothing parameter scaling rules such as attenuation-dependent scaling. Notably, either image-derived or population-based blood input functions can be used with this method.

FIG. 1 shows reconstruction of dynamic emission images $100b$ (herein referred to as "dynamic images $100b$") and parametric fitting of the emission images $100b$ to generate parametric images $100c$, according to an embodiment of the present disclosure. As previously described, the dynamic images $100b$ can be reconstructed frame-by-frame from dynamic sinogram data $100a$. The parametric images $100c$ can be generated by performing Patlak analysis on the TAC pixel-by-pixel (or voxel-by-voxel) to estimate the parametric images $100c$. This indirect method is sensitive to the noise, which degrades the image quality in the parametric images $100c$ since the spatial information embedded in the dynamic PET data is disregarded in the Patlak analysis.

In some embodiments, given a set of measured dynamic sinogram data $100a$ including T frames where $y=[y'_1, y'_2, \ldots, y_T']'$, the reconstructed image $\widehat{x_n}$ is generated by solving the optimization problem:

$$\hat{x}_n(y_n) = \arg\max_{x_n \geq 0}[L(y_n \mid x_n) - \beta_n \phi(x_n)],$$

wherein $y_n$ is the measured sinogram for frame n, $x_n$ is the unknown radioactive tracer/activity distribution, $L(y_n|x_n)$ is the log likelihood function, $\phi(x_n)$ is the penalty function (also referred to as a regularization function or regularizer), and $\beta_n$ is the penalty parameter that controls the degree of penalty (also referred to as a regularization strength). In the above objective function, $L(y_n|x_n)$ is the data-fidelity term. The penalty parameter $\beta_n$ provides the relative weight between the data-fidelity regularization and terms. For example, when the penalty term penalizes variations/noise in the reconstructed PET image, increasing the value of the penalty parameter $\beta_n$ increases the degree of smoothing, reducing both the noise level and the resolution.

With the frame-by-frame reconstructed images $\hat{x}=[\widehat{x_1}, \widehat{x_2}, \ldots, \widehat{x_T}]'$, the Patlak parametric images can be estimated pixel-by-pixel (or voxel-by-voxel) using least squares estimation with regularization as follows:

$$\begin{bmatrix} \hat{\kappa} \\ \hat{b} \end{bmatrix} = \arg\min_{k, b \geq 0}\left[\frac{1}{2}\left\|\hat{x} - (A \otimes I_T)\begin{bmatrix} \kappa \\ b \end{bmatrix}\right\|^2 + \beta_k \phi(\kappa) + \beta_b \phi(b)\right],$$

where $\kappa$ and $b$ are the parametric images of the Patlak slope and Patlak intercept, respectively, A is composed by the blood input function and its integral for frame 1 to T, $\otimes$ denotes the Kronecker product, $I_T$ is an identity matrix, and $\beta_\kappa$ and $\beta_b$ are the parameters controlling the degree of penalty on the parametric images.

In some embodiments, the penalty function can be a patch-based edge-preserving penalty function, which uses neighboring patches instead of individual pixels/voxels to compute the penalty as exemplified by the expression:

$$\phi(x) = \sum_{j=1}^{N} \sum_{l \in N_j} \gamma_{jl} \psi(|f_j(x) - f_l(x)|),$$

wherein the l-e-2 norm or Euclidean distance, which is given by $$|f_j(x) - f_l(x)| = \sqrt{\sum_{k=1}^{n_k} (x_{jk} - x_{lk})^2},$$

can be the measure of distance between the patches of pixels/voxels surrounding pixel/voxel j and pixel/voxel l, $N_j=\{x_{j1}, x_{j2}, \ldots, x_{1jk}\}$ denotes the neighborhood of pixel/voxel j, $\gamma_{jl}$ is the weight related to the distance between pixel/voxel j and pixel/voxel l, and $\psi(\cdot)$ is the potential function, which is given by $$\psi(t) = \delta\left(\frac{|t|}{\delta} - \log\left(1 + \frac{|t|}{\delta}\right)\right),$$

where $\delta$ is a position-dependent penalty parameter that controls the shape of the potential function and the extent of edge-preservation.

The penalty function discussed above is straightforward to generalize and can be applied for both pairwise and patch-based penalties, as would be understood by a person of ordinary skill in the art. Other penalty functions can be used without departing from the spirit of the methods described herein, as would be understood by a person of ordinary skill in the art. For example, the total variation minimization (TV) penalty function penalizes solutions for which the total variation is large. TV regularization is one non-limiting example of many different types of regularization penalties that can be used without departing from the spirit of the methods described herein. Other non-limiting examples of regularization penalties included, e.g., a Huber penalty, a broken parabola penalty, quadratic penalties, non-quadratic penalties, etc.

By increasing the magnitude of the penalty parameter $\beta_n$, noise in the reconstructed image is suppressed while reducing resolution. Accordingly, regions having lower activity can benefit from a higher degree of smoothing because the count statistics in these regions make them more prone to a low signal-to-noise ratio (SNR) (i.e., relatively high noise levels) and fine resolution in these regions is likely not required. For example, higher tracer densities and activity levels are generally found near the region of interest (e.g., due to higher metabolic rates of a lesion). Thus, image reconstruction in which lower activity corresponds to a larger penalty parameter $\beta_n$ can be beneficial.

Additionally, where the activity is high, a lower penalty parameter $\beta_n$ can prevent reduced resolution without sacrificing image quality because the signal is already large compared to the noise. Thus, in these regions of high activity, the SNR can be already sufficiently high without the increased smoothing provided by a large value for the penalty parameter $\beta_n$.

Figure 2:
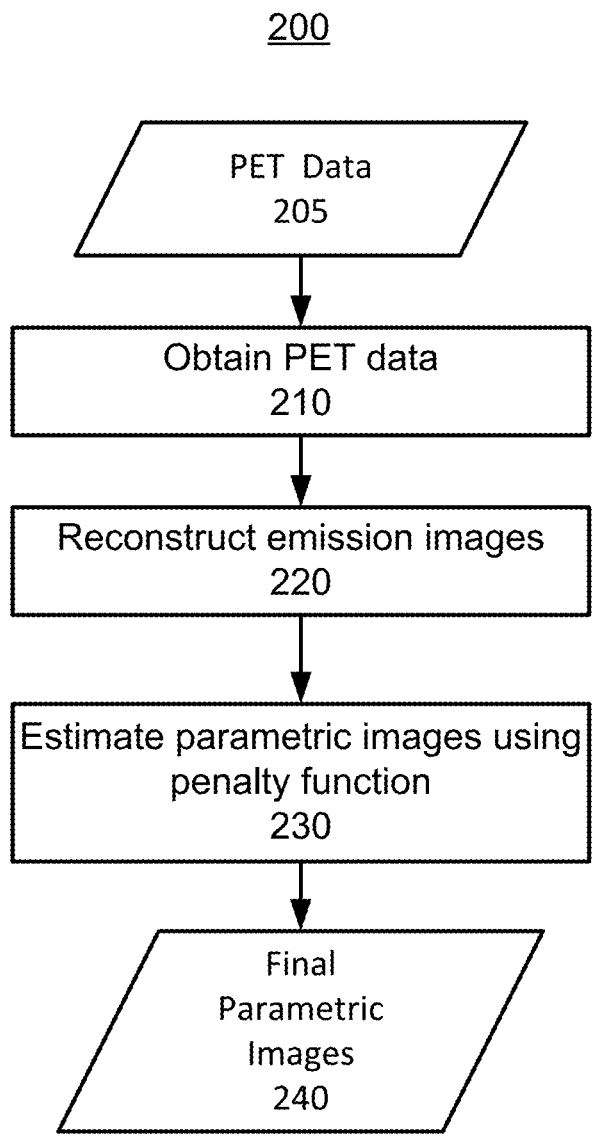
FIG. 2 shows a non-limiting example of a flow chart for a method of imaging, according to an embodiment of the present disclosure.

FIG. 2 shows a non-limiting example of a flow chart for performing the methods described herein, according to an embodiment of the present disclosure. In an embodiment, the parameters/type of the penalty can depend on a spatial variations in the activity level, which is derived from the reconstructed image itself, allowing, e.g., more smoothing in regions of low activity and less smoothing and/or more edge enhancement in regions of greater activity. In some embodiments, the penalty type, one or more penalty parameter (e.g., a parameter controlling the edge enhancement penalty/shape), and the penalty strength can each be based on an initially estimated activity map (e.g., a preliminary reconstructed PET image). The optimal degree of penalty can depend the level of activity in a given image. That is, different images with different amounts of activity can benefit from having different degrees of penalty. Further, this idea can carryover and apply to different regions within an image. That is, a region with a greater level of activity can benefit from a different degree of penalty than a region with a lesser level of activity. Since different organs have different background activity levels, the penalty parameter can be position dependent (e.g., organ-activity dependent) in addition to being PET scan dependent (e.g., image and/or acquisition time dependent).

In FIG. 2, method 200 begins at step 210 by obtaining emission data 205 for tomographic reconstruction of a PET image. For example, incident radiation (e.g. gamma rays) incident on an array of scintillator crystals are converted to scintillation photons, which are in turn converted to photoelectrons by photodetectors. Further, in some embodiments, the photoelectron signals from the photodetectors can be amplified, pulse-shaped, filtered, and otherwise pre-conditioned and processed before being digitized using a data acquisition system (DAS) as time, energy, and position information for respective counts and/or coincidence pairs and then stored to a non-transitory computer readable memory. The PET data 205 can then be obtained from the memory in preparation for tomographic image reconstruction.

In some embodiments, the PET data 205 can be counts that are pre-processed, calibrated, and/or arranged into a sinogram format (e.g., a histogram of counts). In some embodiments, pre-processing can include position corrections, energy corrections, timing corrections, etc. Further, the emission data 205 can be corrected for sensitivity using various calibration and geometric factors. Moreover, the pre-processing can include corrections for a detector offset and gain, variations in quantum efficiency in the detectors, etc. Further, these corrections can be based on calibration data, empirical, and known parameters.

In step 220, an initial PET image is reconstructed. For example, the PET data 205 is used to reconstruct an image of radioactivity level (e.g., tracer density) as a function of voxel position. The image reconstruction can be performed using a back-projection method, a filtered back-projection method, a Fourier-transform-based image reconstruction method, an iterative image reconstruction method, a matrix-inversion image reconstruction method, a statistical image reconstruction method, a list-mode method, or other reconstruction method or combination thereof, as would be understood as a person of ordinary skill in the art.

In step 220, the activity map is determined from the initial PET image, but the activity map is not necessarily identical with the initial PET image. In an embodiment, given measured dynamic sinogram data $100a[y'_1, y'_2, \ldots, y'_T]'$ including T frames, the dynamic sinogram data $100a$ can be summed together into $y=y_1+y_2+ \ldots +y_T$. An ordered subset expectation maximization (OSEM) iteration can then be performed on the summed dynamic sinogram data $100a$ to estimate the activity map $X_{OSEM}$.

In some embodiments, the fine resolution is not required for the spatial variation of the penalty. For example, the activity map can be based on a smoothed or coarse-grained version of the initial PET image in which a low-spatial-frequency filter has been applied to the initial PET image. Also, other denoising methods could be applied to mitigate the effect of noise on the activity map and the spatial variation of the penalty.

Exemplary denoising methods include linear smoothing filters, anisotropic diffusion, non-local means, or nonlinear filters. Linear smoothing filters remove noise by convolving the original image with a mask that represents a low-pass filter or smoothing operation. For example, the Gaussian mask comprises elements determined by a Gaussian function. This convolution brings the value of each pixel/voxel into closer agreement with the values of its neighbors. Anisotropic diffusion removes noise while preserving sharp edges by evolving an image under a smoothing partial differential equation similar to the heat equation. A median filter is an example of a nonlinear filter and, if properly designed, a nonlinear filter can also preserve edges and avoid blurring. The median filter is one example of a rank-conditioned rank-selection (RCRS) filter, which can be applied to remove salt and pepper noise from an image without introducing significant blurring artifacts. Additionally, a filter using a total-variation (TV) minimization regularization term can be applied if imaged region supports an assumption of uniformity over large areas that are demarked by sharp boundaries between the uniform areas. A TV filter is another example of a nonlinear filter. Moreover, non-local means filtering is an exemplary method of determining denoised pixels/voxels using a weighted average over similar patches within the images.

In step 230, the parametric images $100c$ can be estimated while incorporating the penalty function. In an embodiment, the dynamic images $100b$ can be analyzed to generate the TAC for each dynamic image $100b$. Final parametric images 240 can be generated by performing Patlak analysis on the TAC for the each dynamic image $100b$ in a pixel-by-pixel (or voxel-by-voxel) manner to estimate the final parametric images 240. The Patlak parametric images can be estimated pixel-by-pixel (or voxel-by-voxel) from the frame-by-frame reconstructed images $\hat{x}$, for example, using a least squares estimation.

The Patlak parametric images can be described by $\kappa$ (the parametric images of the Patlak slope) and $b$ (the parametric images of the Patlak intercept). The penalty can be described by $\beta_\kappa$ and $\beta_b$, the parameters controlling the degree of penalty on the parametric images. In some embodiments, the spatial variation in the penalty arises from the regularization of $\beta_n$, $\beta_\kappa$, and $\beta_b$ being position dependent. The position dependence of the penalty terms $\beta_n$, $\beta_\kappa$, and $\beta_b$ can be referred to as a $\beta$-map, and can be represented as $\beta_j$ in which the subscript j is the index of the $j^{th}$ voxel/pixel in the reconstructed PET image $x_{OSEM}$. The $\beta$-map can be scaled according to $\beta_j = f(xj_{OSEM})$ for each pixel/voxel j, where $f(\bullet)$ can be any user-selected function. For example, the user-selected function $f(\bullet)$ can include smoothing, low-frequency filtering, and/or denoising, as discussed above.

The developed $\beta$-map can be applied in the regularization of frame-by-frame reconstruction where for each frame n, $\beta_{nj} = f_n(xj_{OSEM})$ and Patlak model fitting where $\beta_{\kappa j} = f_\kappa(xj_{OSEM})$, $\beta_{bj} = f_b(xj_{OSEM})$. The same scaling rule can also be applied to $\delta$, the penalty parameter that controls the shape of the potential function and the extent of edge-preservation, such that $\delta_j = g(xj_{OSEM})$ and applied in the frame-by-frame reconstruction and Patlak fitting. Notably, either image-derived or population-based blood input function can be used for Patlak fitting. It may be appreciated that any globally convergent numerical optimization algorithm can be used to find the optimizer of the final cost function (with convex penalties).

Advantageously, the method 200 provides different penalty parameters in dynamic PET reconstruction, both for frame-by-frame reconstruction of the dynamic images $100b$ and the Patlak fitting for the generation of the parametric images $100c$. Notably, the method 200 utilizes spatially varying penalty parameter tuning guided by the static reconstruction of the data itself. The method 200 thus provides a user full flexibility in choosing the smoothing and edge-preservation strengths according to any desired function of activity estimates, which allows patient-adaptive optimization of reconstruction methods for specific tasks in routine clinical settings.

Figure 3A:
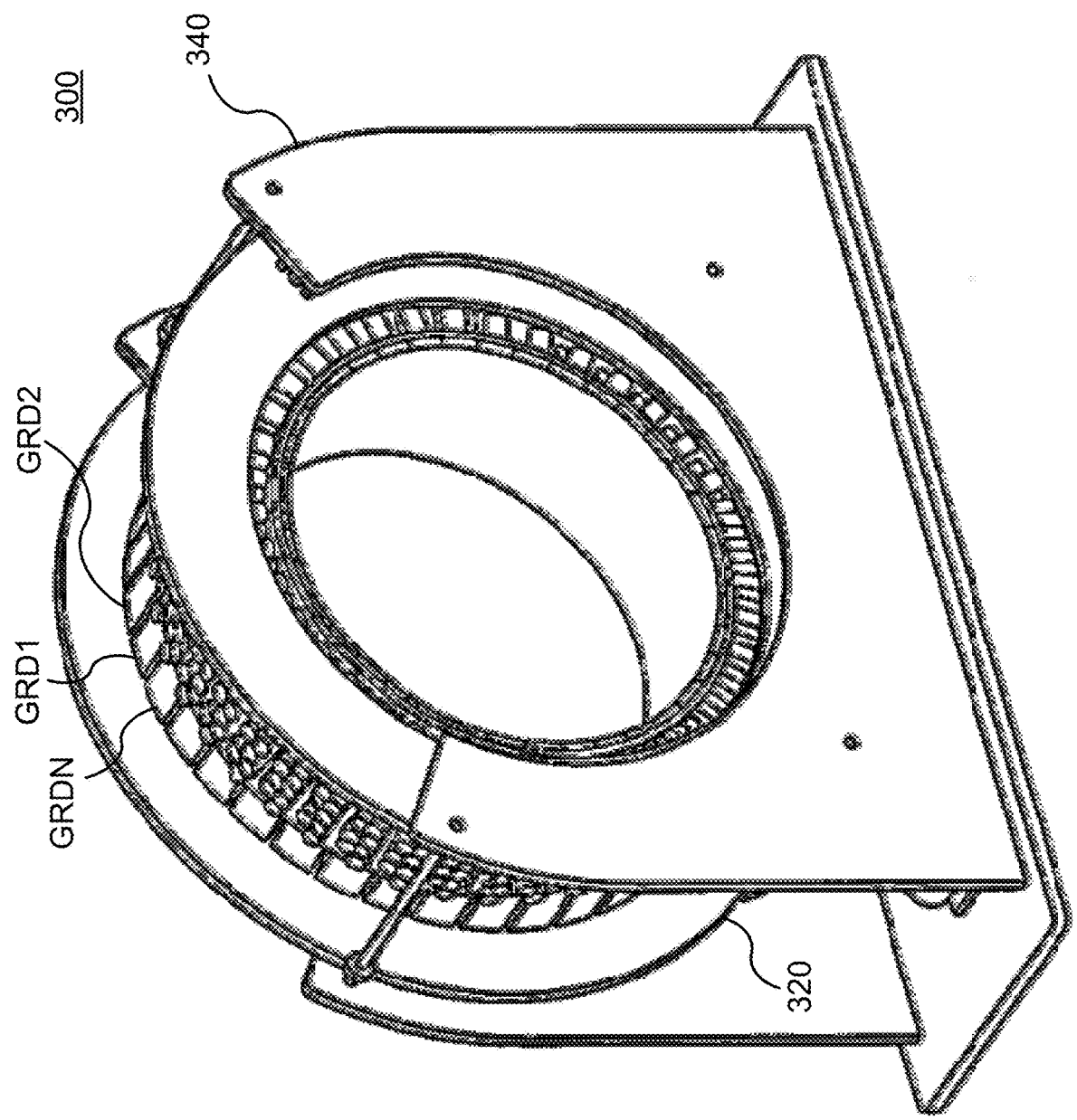
FIG. 3A shows a perspective view of a positron-emission tomography (PET) scanner, according to an embodiment of the present disclosure.

FIGS. 3A and 3B show a non-limiting example of a PET scanner 300 that can implement the methods 100 and 200. The PET scanner 300 includes a number of gamma-ray detectors (GRDs) (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 300.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs.

Alternatively, the scintillation photons can be detected by an array a silicon photomultipliers (SiPMs), and each individual detector crystals can have a respective SiPM.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

FIG. 3B shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 3A and 3B. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 3B shows an example of the arrangement of the PET scanner 300, in which the object OBJ to be imaged rests on a table 316 and the GRD modules GRD1 through GRDN are arranged circumferentially around the object OBJ and the table 316. The GRDs can be fixedly connected to a circular component 320 that is fixedly connected to the gantry 340. The gantry 340 houses many parts of the PET imager. The gantry 340 of the PET imager also includes an open aperture through which the object OBJ and the table 316 can pass, and gamma-rays emitted in opposite directions from the object OBJ due to an annihilation event can be detected by the GRDs and timing and energy information can be used to determine coincidences for gamma-ray pairs.

In FIG. 3B, circuitry and hardware is also shown for acquiring, storing, processing, and distributing gamma-ray detection data. The circuitry and hardware include: a processor 370, a network controller 374, a memory 378, and a data acquisition system (DAS) 376. The PET imager also includes a data channel that routes detection measurement results from the GRDs to the DAS 376, the processor 370, the memory 378, and the network controller 374. The DAS 376 can control the acquisition, digitization, and routing of the detection data from the detectors. In one implementation, the DAS 376 controls the movement of the bed 316. The processor 370 performs functions including reconstructing images from the detection data, pre-reconstruction processing of the detection data, and post-reconstruction processing of the image data, as discussed herein.

The processor 370 can be configured to perform various steps of methods 100 and/or 200 described herein and variations thereof. The processor 370 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 370 can execute a computer program including a set of computer-readable instructions that perform various steps of method 100 and/or method 200, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 378 can be a hard disk drive, CD-ROM drive, DVD drive, FLASH drive, RAM, ROM or any other electronic storage known in the art.

The network controller 374, such as an Intel Ethernet PRO network interface card from Intel Corporation of America, can interface between the various parts of the PET imager. Additionally, the network controller 374 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In the preceding description, specific details have been set forth, such as a particular geometry of a processing system and descriptions of various components and processes used therein. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

Embodiments of the present disclosure may also be as set forth in the following parentheticals.

(1) An apparatus, comprising processing circuitry configured to obtain a plurality of dynamic sinograms, each of the plurality of dynamic sinograms representing detection events of gamma rays at a plurality of detector elements, sum the plurality of dynamic sinograms to generate an activity map based on a radioactivity level of the gamma rays, reconstruct, using the plurality of dynamic sinograms, a plurality of dynamic images, each of the plurality of dynamic images corresponding to one of the each of the plurality of dynamic sinograms, and generate, using the plurality of dynamic sinograms and the activity map, at least one parametric image.

(2) The apparatus of (1), wherein the circuitry is further configured to generate a time activity curve for the each of the plurality of dynamic images, and the at least one parametric image is generated using the activity map and the time activity curve for the each of the plurality of dynamic images.

(3) The apparatus of (2), wherein the circuitry is further configured to generate the at least one parametric image using an objective function including a penalty term, wherein the penalty term includes one or more spatially-varying smoothing parameters determined from the activity map.

(4) The apparatus of (3), wherein the penalty term includes a first parameter controlling the degree of penalty based on a Patlak slope of the time activity curve, and a second parameter controlling the degree of penalty based on a Patlak intercept of the time activity curve.

(5) The apparatus of any one of (2) to (4), wherein the circuitry is further configured to generate the at least one parametric image using an objective function including a penalty term, wherein the penalty term includes an edge-preserving potential function that has a shape based on the activity map.

(6) The apparatus of any one of (1) to (5), wherein the circuitry is further configured to generate the at least one parametric image using a voxel-by-voxel parametric fitting for the each of the plurality of dynamic sinograms.

(7) The apparatus of any one of (1) to (6), further comprising a detector including the plurality of detector elements configured to detect the gamma rays generated from a tracer.

(8) The apparatus of any one of (1) to (7), wherein the activity map is generated using an ordered-subset expectation maximization (OSEM) method, which is iteratively repeated until a predetermined stopping criteria is reached.

(9) The apparatus of any one of (1) to (8), wherein the dynamic sinograms are obtained over a predetermined duration of time at predetermined intervals.

(10) The apparatus of any one of (1) to (9), wherein the circuitry is further configured to segment the activity map based on types of organs represented therein, and generate the at least one parametric image, wherein the penalty term is based on the segmentation of the activity map.

(11) A method of imaging, comprising obtaining a plurality of dynamic sinograms, each dynamic sinogram representing detection events of gamma rays at a plurality of detector elements; summing the plurality of dynamic sinograms to generate an activity map based on a radioactivity level of the gamma rays; reconstructing, using the plurality of dynamic sinograms, a plurality of dynamic images, each of the plurality of dynamic images corresponding to one of the each of the plurality of dynamic sinograms; and generating, using the plurality of dynamic sinograms and the activity map, at least one parametric image.

(12) The method of (11), further comprising generating a time activity curve for the each of the plurality of dynamic images, wherein the at least one parametric image is generated using the activity map and the time activity curve for the each of the plurality of dynamic images.

(13) The method of (12), wherein the generating the at least one parametric image further includes using an objective function including a penalty term, the penalty term including one or more spatially-varying smoothing parameters determined from the activity map.

(14) The method of (13), wherein the penalty term includes a first parameter controlling the degree of penalty based on a Patlak slope of the time activity curve, and a second parameter controlling the degree of penalty based on a Patlak intercept of the time activity curve.

(15) The method of any one of (12) to (14), wherein the generating the at least one parametric image further includes using an objective function including a penalty term, wherein the penalty term includes an edge-preserving potential function that has a shape based on the activity map.

(16) The method of any one of (11) to (15), wherein the generating the at least one parametric image further includes using a voxel-by-voxel parametric fitting for the each of the plurality of dynamic sinograms.

(17) The method of any one of (11) to (16), wherein the parametric fitting uses a least squares estimation.

(18) The method of any one of (11) to (17), wherein the activity map is generated using an ordered-subset expectation maximization (OSEM) method, which is iteratively repeated until a predetermined stopping criteria is reached.

(19) The method of any one of (11) to (18), further comprising segmenting the activity map based on types of organs represented therein; and generating the at least one parametric image, wherein the penalty term is based on the segmentation of the activity map.

(20) A non-transitory computer-readable storage medium including executable instructions, which when executed by circuitry, cause the circuitry to perform the method comprising obtaining a plurality of dynamic sinograms, each dynamic sinogram representing detection events of gamma rays at a plurality of detector elements; summing the plurality of dynamic sinograms to generate an activity map based on a radioactivity level of the gamma rays; reconstructing, using the plurality of dynamic sinograms, a plurality of dynamic images, each of the plurality of dynamic images corresponding to one of the each of the plurality of dynamic sinograms; and generating, using the plurality of dynamic sinograms and the activity map, at least one parametric image.

What is claimed is:

1. An apparatus, comprising:
    processing circuitry configured to
        obtain a plurality of dynamic sinograms, each of the plurality of dynamic sinograms representing detection events of gamma rays at a plurality of detector elements,
        sum the plurality of dynamic sinograms to generate an activity map based on a radioactivity level of the gamma rays,
        reconstruct, using the plurality of dynamic sinograms, a plurality of dynamic images, each of the plurality of dynamic images corresponding to one of the each of the plurality of dynamic sinograms, and
        generate, using the plurality of dynamic sinograms and the activity map, at least one parametric image.

2. The apparatus of claim 1, wherein the circuitry is further configured to generate a time activity curve for the each of the plurality of dynamic images, and the at least one parametric image is generated using the activity map and the time activity curve for the each of the plurality of dynamic images.

3. The apparatus of claim 2, wherein the circuitry is further configured to generate the at least one parametric image using an objective function including a penalty term, wherein the penalty term includes one or more spatially-varying smoothing parameters determined from the activity map.

4. The apparatus of claim 3, wherein the penalty term includes a first parameter controlling the degree of penalty based on a Patlak slope of the time activity curve, and a second parameter controlling the degree of penalty based on a Patlak intercept of the time activity curve.

5. The apparatus of claim 3, wherein the circuitry is further configured to
segment the activity map based on types of organs represented therein, and
generate the at least one parametric image, wherein the penalty term is based on the segmentation of the activity map.

6. The apparatus of claim 2, wherein the circuitry is further configured to generate the at least one parametric image using an objective function including a penalty term, wherein the penalty term includes an edge-preserving potential function that has a shape based on the activity map.

7. The apparatus of claim 1, wherein the circuitry is further configured to generate the at least one parametric image using a voxel-by-voxel parametric fitting for the each of the plurality of dynamic sinograms.

8. The apparatus of claim 1, further comprising:
a detector including the plurality of detector elements configured to detect the gamma rays generated from a tracer.

9. The apparatus of claim 1, wherein the activity map is generated using an ordered-subset expectation maximization (OSEM) method, which is iteratively repeated until a predetermined stopping criteria is reached.

10. The apparatus of claim 1, wherein the dynamic sinograms are obtained over a predetermined duration of time at predetermined intervals.

11. A method of imaging, comprising:
obtaining a plurality of dynamic sinograms, each dynamic sinogram representing detection events of gamma rays at a plurality of detector elements;
summing the plurality of dynamic sinograms to generate an activity map based on a radioactivity level of the gamma rays;
reconstructing, using the plurality of dynamic sinograms, a plurality of dynamic images, each of the plurality of dynamic images corresponding to one of the each of the plurality of dynamic sinograms; and
generating, using the plurality of dynamic sinograms and the activity map, at least one parametric image.

12. The method of claim 11, further comprising:
generating a time activity curve for the each of the plurality of dynamic images, wherein
the at least one parametric image is generated using the activity map and the time activity curve for the each of the plurality of dynamic images.

13. The method of claim 12, wherein the generating the at least one parametric image further includes using an objective function including a penalty term, the penalty term including one or more spatially-varying smoothing parameters determined from the activity map.

14. The method of claim 13, wherein the penalty term includes a first parameter controlling the degree of penalty based on a Patlak slope of the time activity curve, and a second parameter controlling the degree of penalty based on a Patlak intercept of the time activity curve.

15. The method of claim 13, further comprising:
segmenting the activity map based on types of organs represented therein; and
generating the at least one parametric image, wherein the penalty term is based on the segmentation of the activity map.

16. The method of claim 12, wherein the generating the at least one parametric image further includes using an objective function including a penalty term, wherein the penalty term includes an edge-preserving potential function that has a shape based on the activity map.

17. The method of claim 11, wherein the generating the at least one parametric image further includes using a voxel-by-voxel parametric fitting for the each of the plurality of dynamic sinograms.

18. The method of claim 17, wherein the parametric fitting uses a least squares estimation.

19. The method of claim 11, wherein the activity map is generated using an ordered-subset expectation maximization (OSEM) method, which is iteratively repeated until a predetermined stopping criteria is reached.

20. A non-transitory computer-readable storage medium including executable instructions, which when executed by circuitry, cause the circuitry to perform the method according to claim 11.

* * * * *